United States Patent
Schreck et al.

(10) Patent No.: US 9,120,806 B2
(45) Date of Patent: Sep. 1, 2015

(54) DIANHYDROSUGAR PRODUCTION PROCESS

(75) Inventors: David James Schreck, Lake City, MN (US); Marion McKinley Bradford, Hendersonville, NC (US); Nye Atwood Clinton, Hurricane, WV (US); Paul Aubry, Hurricane, WV (US)

(73) Assignee: Iowa Corn Promotion Board, Johnston, IA (US)

( * ) Notice: Subject to any disclaimer, the term of this patent is extended or adjusted under 35 U.S.C. 154(b) by 245 days.

(21) Appl. No.: 12/421,514

(22) Filed: Apr. 9, 2009

(65) Prior Publication Data

US 2009/0259057 A1    Oct. 15, 2009

Related U.S. Application Data

(60) Provisional application No. 61/043,939, filed on Apr. 10, 2009.

(51) Int. Cl.
*C07D 493/04* (2006.01)
*C07D 493/02* (2006.01)

(52) U.S. Cl.
CPC .................................. *C07D 493/04* (2013.01)

(58) Field of Classification Search
USPC .......................................... 536/124; 549/464
See application file for complete search history.

(56) References Cited

U.S. PATENT DOCUMENTS

| | | | |
|---|---|---|---|
| 3,454,603 | A | 7/1969 | Hartman |
| 4,313,884 | A | 2/1982 | Arena |
| 4,408,061 | A | 10/1983 | Salzburg et al. |
| 4,506,086 | A * | 3/1985 | Salzburg et al. ............. 549/464 |
| 4,564,692 | A | 1/1986 | Feldmann et al. |
| 4,659,846 | A | 4/1987 | Maurer et al. |
| 4,861,513 | A | 8/1989 | Lueders |
| 6,407,266 | B2 | 6/2002 | Bhatia |
| 6,639,067 | B1 | 10/2003 | Brinegar et al. |
| 6,670,033 | B1 | 12/2003 | Hubbard et al. |
| 6,689,892 | B2 * | 2/2004 | Andrews et al. ............. 549/464 |
| 6,818,781 | B2 * | 11/2004 | Bhatia ......................... 549/465 |
| 6,831,181 | B2 | 12/2004 | Bhatia |
| 6,849,748 | B2 | 2/2005 | Moore et al. |
| 6,864,378 | B2 | 3/2005 | Bhatia |
| 7,122,661 | B2 | 10/2006 | Fleche et al. |
| 7,420,067 | B2 | 9/2008 | Sanborn |
| 2002/0028959 | A1 | 3/2002 | Andrews et al. |
| 2004/0013217 | A1 | 1/2004 | Dietrich et al. |
| 2004/0030161 | A1 | 2/2004 | Bhatia |
| 2004/0110969 | A1 | 6/2004 | Fleche et al. |
| 2007/0173652 | A1 | 7/2007 | Holladay et al. |

FOREIGN PATENT DOCUMENTS

| | | | |
|---|---|---|---|
| WO | 00/14081 A1 | 3/2000 | |
| WO | WO 00/14081 | * 3/2000 | ........... C07D 307/02 |

OTHER PUBLICATIONS

Ault, Techniques and Experiments for Organic Chemistry, 2nd Ed, Holbrook, 1976, p. 73.*
Fleche et al, Starch/Starke, 1986, 38(1), 26-30.*
Sciencelab.com, created 2005, pp. 1-7.*
Barker, Robert, Conversion of Acyclic Carbohydrates into Tetrahydrofuran Derivatives. Acid-Catalyzed Dehydration of Hexitols, J. Org. Chem., Feb. 1970, vol. 35, No. 2, pp. 461-464.
Hockett, et al., Hexitol Anhydrides. The Structures of the Anhydromannitols of Brigl and Gruner. The Structure of Isomannide, Am. Chem. So. Jun. 1946, vol. 68., pp. 930-935.
Soltzberg, et al., Hexitol Anhydrides. Synthesis and Structure of Arlitan, the 1, 4-Monoanhydride of Sorbitol, J. Am. Chem. Soc., Jun. 18, 1946, vol. 68, No. 6, pp. 919-921.
Fleche, et al., Isosorbide Preparation, Properties and Chemistry, Starch/Starke, 1986, vol. 38(c), pp. 26-30.
Goodwin, et al., Preparation of bicyclic hexitol anhydrides by using acidic cation-exchange resin in a binary solvent. 13 C-N.m.r. spectroscopy confirms configurational inversion in chloride displacement of methanesulfonate in isomannide and isosorbide derivatives, Carbohdrate Res., 1980, vol. 79, pp. 133-141.
Bock, Klaus; Pedersen, Christian; Thogersen, Henning: Acid Catalyzed Dehydration of Alditols. Part I. D-Glucitol and D-Mannitol. Acta Chem. Scand. B 35, 441-449 (1981).

* cited by examiner

*Primary Examiner* — Ganapathy Krishnan
(74) *Attorney, Agent, or Firm* — Davis, Brown, Koehn, Shors & Roberts, P.C.; Kent A. Herink (57) ABSTRACT

An enhanced process for the production of a dianhydrosugar, such as isosorbide, from the corresponding sugar alcohol is described. The sugar alcohol is combined with an acid catalyst and reacted at elevated temperatures and at atmospheric pressure, eliminating the need for a vacuum. High selectivity and yields are achieved.

15 Claims, 5 Drawing Sheets

DIANHYDROSUGAR PRODUCTION PROCESS

This application claims priority to U.S. Patent Application Ser. No. 61/043,939, filed Apr. 10, 2008.

BACKGROUND OF THE INVENTION

The invention relates generally to methods for producing dianhydrosugars and, more specifically, to an improved method for producing isosorbide from sorbitol at ambient pressures.

The production of anhydrosugars from sorbitol and similar sugar alcohols has been referenced in the patent literature for many years. The earliest work, in 1884, was done on 1,4:3, 6-dianhydro-D-mannitol by Fauconnier. Interest has grown since then as a large body of chemical literature has developed in this area around production of isosorbide.

The 1,5:3,6-dianhydrohexitols, of which isosorbide is an example, are derived from natural products. Therefore, these compounds are classified as "renewable resources." Furthermore, 1,4:3,6-dianhydrohexitols, such as isosorbide, can be used as starting materials and intermediates in chemical reactions. For example, isosorbide is reported to be useful in the production of pharmaceutical compounds, plastic and polymer production, and in other commercial uses such as in the production of polyurethane, polycarbonates, and polyesters.

Of the known isohexides, isosorbide is considered to be that of the highest importance. Acid catalysts are generally used for dehydrating the sugar alcohol starting material. Many catalysts and reaction conditions have been the subject of claims on improvements in its production. Examples of these are laid out below.

Several processes for the production of anhydrosugar alcohols (including isohexides such as isosorbide) are known. See, for example, U.S. Pat. No. 6,639,067 wherein a process is described for production of isosorbide that requires the use of an organic solvent. Alternatively U.S. Pat. No. 6,849,748 discloses a route to isosorbide that does not require an organic solvent but prefers a reaction run under reduced pressure to achieve good conversion of the starting sugar alcohol. PCT application number PCT/US99/00537 (WO 00/14081), discloses a continuous production method with recycling of organic solvent.

Various processes are known for producing anhydro-polyls starting from D-sorbitol (see e.g. B. R. Barker, J. Org. Chem., 35, 461 (1970), J. Feldmann et al., EP-OS 0 052 295 and DE-OS 30 14 626, Soltzberg et al., J. Am. Chem. Soc., 68, 919, 927, 930 (1946) and S. Ropuszinski et al., Prozed. Chem., 48, 665 (1969)). In all these processes water is generated in the presence of an acid catalyst and at a raised temperature. As the reaction progresses, the concentration of dianhydrosorbitol increases, while that of sorbitol decreases.

Most methods involve the use of concentrated acids and organic solvents. Goodwin et al. (Carbohydrate Res. 79 (1980), 133-141) have disclosed a method involving the use of acidic-cation-exchange resin in place of concentrated, corrosive acids, but with low yield of isosorbide product. However, a need continues in the art for a process for production of very pure isosorbide, at reasonable yields with inexpensive catalysts, and preferably without the use of potentially hazardous organic solvents or the use of expensive vacuum reactors.

Anhydro sugar alcohols are produced by dehydration of the corresponding sugar alcohols (or monoanhydro sugar alcohols) by the action of various dehydration catalysts, typically strong acid catalysts. Examples of these catalysts include sulfonated polystyrenes ($H^+$ form) and various mineral acids of which sulfuric acid is the most popular.

In particular, a batch process for the formation of the dianhydro sugar alcohol isosorbide has been described as a two-step process involving intramolecular dehydration of sorbitol to sorbitan (1,4-monoanhydrosorbitol), and further reaction of sorbitan to isosorbide (1,4:3,6-dianhydrosorbitol) in an acid catalyzed dehydration-cyclization. In this process, an aqueous solution of sorbitol is charged to a batch reactor. The temperature is increased to 130° C.-135° C. under vacuum (35 mm Hg) to remove the water. When the sorbitol melt is free of water, a catalyst, usually sulfuric acid, is added and the temperature and vacuum levels are maintained. The operable temperature range of the reaction is very narrow. Higher temperatures lead to decomposition and charring of the end product, while lower temperatures inhibit the reaction rate due to difficulties in removal of the water of reaction. This reaction produces isosorbide and a higher molecular weight byproduct. The byproduct is presumably produced by water elimination between two or more sorbitol molecules, but its exact nature is not clearly defined. See G. Flche and M. Huchette, Starch/Starke (1986), 38(c), 26-30 and Roland Beck, Pharm. Mfg Inc. (1996), 97-100. Other monoanhydro byproducts, 2,5-anhydro-L-iditol and 2,5-anhydro-D-mannitol, are also known to be produced under some reaction conditions (Acta. Chem. Scand. B 35, 441-449 (1981)). The use of vacuum adds complexity and cost to the production of isosorbide.

For isosorbide to be used as a monomer in high volume polymers and copolymers, for applications such as containers, it needs to be produced in large quantities, preferably in a continuous process and with low operating costs.

WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel. The large amounts of organic solvent required for such a process make it economically and environmentally undesirable.

U.S. Pat. No. 6,407,266 describes a continuous process in which a process stream containing at least one sugar alcohol or monoanhydro sugar alcohol and, optionally, water is introduced to the first stage of a multistage reactor and then intimately contacted with a countercurrent flow of an inert gas at elevated temperature. This inert gas removes the bulk of any water present in the process stream. This dewatered process stream is then intimately contacted with a dehydration catalyst, with a counter current flow of an inert gas at elevated temperatures to remove water of reaction as formed. Finally, the product is removed from the bottom of the reactor.

The reaction product obtained by processes such as the above, contains about 70 to 80% by weight isosorbide and 20 to 30% undesired reaction byproducts. The reaction product thus needs to be subjected to one or more separation steps, such as evaporation, distillation or chromatographic separation, to isolate the isosorbide. Chromatographic separation is disclosed in U.S. Patent Application No. 60/246,038 (filed 6 Nov. 2000). Separation by vaporization or distillation is difficult because of the low vapor pressure of isosorbide. For example, it has been found that at 140° C., the vapor pressure is only 1.75 mm Hg. Evaporation or distillation at temperatures not much higher than about 140° C. is desirable to minimize product degradation and obtain good purity isosorbide, but the recovery is poor. At higher temperatures, e.g., 170° C., more isosorbide is recovered, but it is of poorer quality.

U.S. Pat. No. 4,564,692 discloses a process using crystallization from aqueous solutions to obtain the high purity needed for applications as polyol components in polyester and polyurethane polymers.

Many of the previous inventions claim the use of a high vacuum to achieve a high degree of water removal to drive the reaction which progresses by the loss of water. A need exists for a continuous process that provides isosorbide in high selectivity at high sorbitol conversion without the high costs associated with running the reaction under high vacuum or the use of organic solvents in the process which increase the operating costs and increase the difficulty of obtaining environmental permits.

In the condensation reaction of sorbitol to 1,4-sorbitan followed by a subsequent condensation reaction to form isosorbide, earlier researchers have proscribed the removal of water to drive the reaction. Most prior art references recommend the use of vacuum to facilitate water removal. The standard preparation of isosorbide has been described in the literature as involving the treatment of sorbitol with sulfuric acid (Hockett, R. C., Fletcher, Jr., J. G., Sheffield, E. L., Goepp, Jr., R. M., Soltzberg, S. J. Am. Chem. So. 1946, 68, 930). The reaction is carried out under vacuum and at elevated temperatures. In the reaction, sorbitol is first converted to either 1,4-soribitan or 3,6-sorbitan, which results in the production of an equivalent of water. The sorbitan is next converted to isosorbide, which again produces an equivalent of water. The water is well known to inhibit the reaction; small amounts of water dramatically impact the reaction rate. The purpose of the vacuum was to remove the water formed during the reaction. Subsequent methods have used a reverse flow of a gas, such as nitrogen, to remove water from the reaction mixture. The need for operating under a vacuum or using a gas stream to remove water adds to the complexity of reactor design as well as operating costs. Surprisingly, we have found that high selectivity and good reaction rates can be achieved at temperatures of around 150° C. and that no vacuum or sparging gas for water removal is required.

SUMMARY OF THE INVENTION

The invention is a method for producing isosorbide from sorbitol without the use of a vacuum to remove water formed during the reaction. The temperature and water content of the reaction mixture are adjusted to control the acid strength in the reaction mixture to provide conditions for high selectivity and productivity of isosorbide.

A purpose of the invention is to provide a fast, selective and productive method for the conversion of sorbitol to isosorbide.

Another purpose of the invention is to provide a method for preparing isosorbide from sorbitol that eliminates the need for a vacuum to remove water from the reaction mixture.

These and other objects of the invention will be understood by those of skill in the art upon a review of this specification.

DESCRIPTION OF THE INVENTION

Each step in the transformation of sorbitol to mannitan (and iditan) or sorbitan, and the conversion of sorbitan to isosorbide, produces an equivalent of water. The reaction scheme is reproduced below (Scheme 1).

Scheme 1

2
1,4-D-Sorbitan

6
D-Isosorbide

The present invention provides an improved process for the production of a dianhydrosugar from a sugar alcohol via the intermediary of the sugar alcohol anhydride. Suitable sugar alcohols include iditol, mannitol and sorbitol.

An acid catalyst is used in the reactions of the present invention. Suitable acid catalysts are those which will catalyze the two condensation reaction steps and which can be effectively removed from the product of the reaction. Suitable catalysts include sulfonated polystyrenes and mineral acids, including sulfuric acid, phosphoric acid; alkyl, aryl, and arylalkylsulfonic acids; polymer bound sulfonic acids; trifluoromethanesulfonic acid; strong acid resins; acid forms of perfluorinated membranes; heteropoly acids and their acidic salts; zeolites; as well as acid clays. The concentration of acid catalyst to be used depends on the particular catalyst selected, the reaction materials and reaction conditions, within the range of between about 0.1% and about 5% and preferably between about 0.5% and 2.5%. Sulfuric acid is the preferred acid catalyst. The preferred concentration of sulfuric acid is between about 0.5% and 2.5% and even more preferably between about 1% and about 2%. Numerous reactions have been practiced within these ranges.

The temperatures at which the reaction is carried out are important. If the reaction temperatures are too low, the rate of the reaction is too slow. If the temperatures are too high, selectivity of the desired dianhydrosugar is reduced. Preferably, the temperature of the reaction is adjusted first to an elevated temperature which produces a satisfactory reaction rate and secondly to remove the water produced in the reaction through evaporation to maintain the acid strength of the acid catalyst at a suitable level. The reaction is carried out at temperatures between about 130° C. and about 170° C., preferably between about 145° C. and about 155° C., and the reaction has been practiced at a variety of temperatures throughout these two ranges. The temperature of the reaction may be ramped over time up from a low temperature to higher temperatures within the previously stated ranges. In addition, the temperature of the reaction when the condensation of the sugar alcohol to the intermediaries dominates may be conducted over one range of temperatures while the temperature of the reaction when the condensation of the intermediaries to the dianhydrosugar dominates may be conducted over a second range of temperatures.

Example 1

Figure 1:
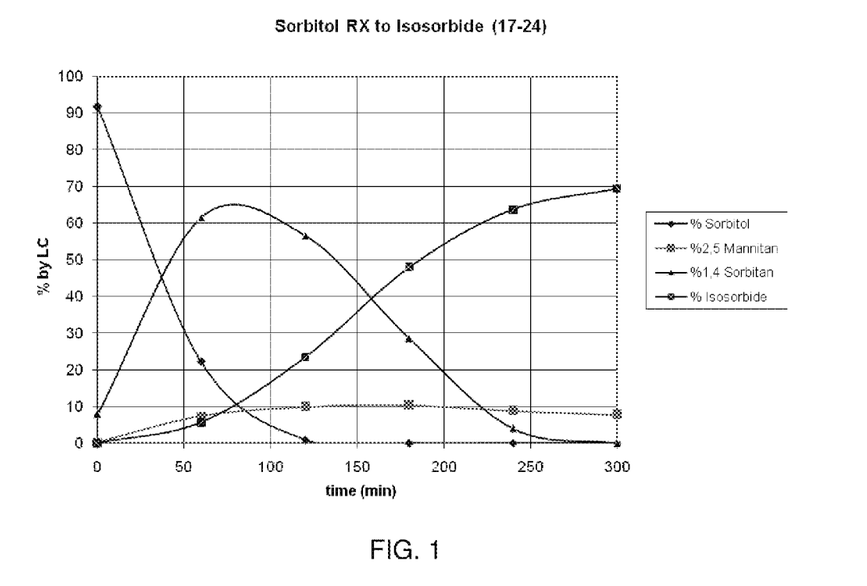
FIG. 1 is a graph over time of the production of isosorbide from sorbitol, including the intermediary sorbitan and the side reaction product, mannitan, run under a vacuum of about 10-20 millibar.

A reaction was carried out wherein sorbitol and sulfuric acid (0.5% by weight of the starting sorbitol) were combined in a reaction vessel. The vessel was heated to 125° C. and run under a vacuum of about 10-20 millibar. Samples of the reaction mixture were taken at regular intervals and assayed for sorbitol, sorbitan, mannitan, and isosorbide. The results are shown in FIG. 1. The sorbitol concentration decreases smoothly as a function of time to approximately zero after about 120 minutes (the sorbitol line is believed to include also mannitol and iditol which, in turn, react to give isomannide or isoidide). The concentration of sorbitan increases and then decreases as it is first condensed from sorbitol and then converted to isosorbide. Isosorbide is formed at a reasonable rate only after significant amounts of sorbitan have been produced. As the sorbitan is consumed, isosorbide becomes the major compound in the reaction mixture. The reaction mixture also contains small amounts of mannitan and iditan.

Example 2

Figure 2:
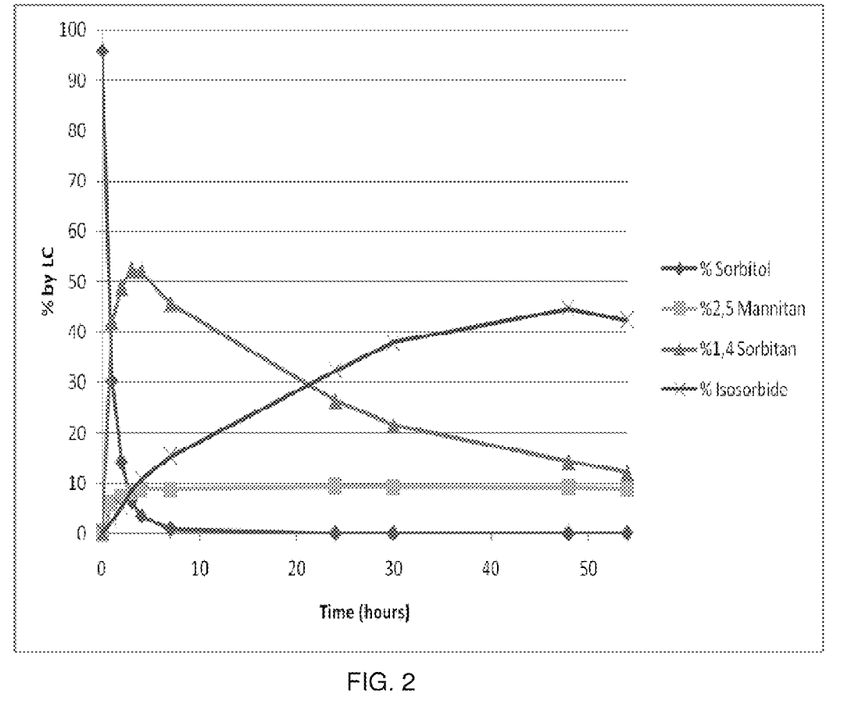
FIG. 2 is a graph of the production of isosorbide from sorbitol, including the intermediary sorbitan and the side reaction product mannitan, run under sealed conditions where no water was allowed to leave the reaction vessel.

Another reaction was carried out wherein 10% water by weight was added to the reaction mixture and the reaction vessel was sealed so that water formed in the various reactions could not escape from the system. Each of the two steps in the reaction forms a further 10% (approximately) water. In this example, the reaction temperature was 150° C. and the acid concentration was 1%. Samples were taken during regular intervals and assayed for sorbitol, sorbitan, mannitan and isosorbide. The results are shown in FIG. 2. Even with the higher temperature and higher starting acid concentration, the reaction is not complete even after 48 hours. This is in contrast to Example 1, run under significantly milder conditions, where the reaction was complete after only about five hours. From FIG. 2, it is seen that even the fast reaction of sorbitol to sorbitan is not complete at five hours.

Example 3

Figure 3:
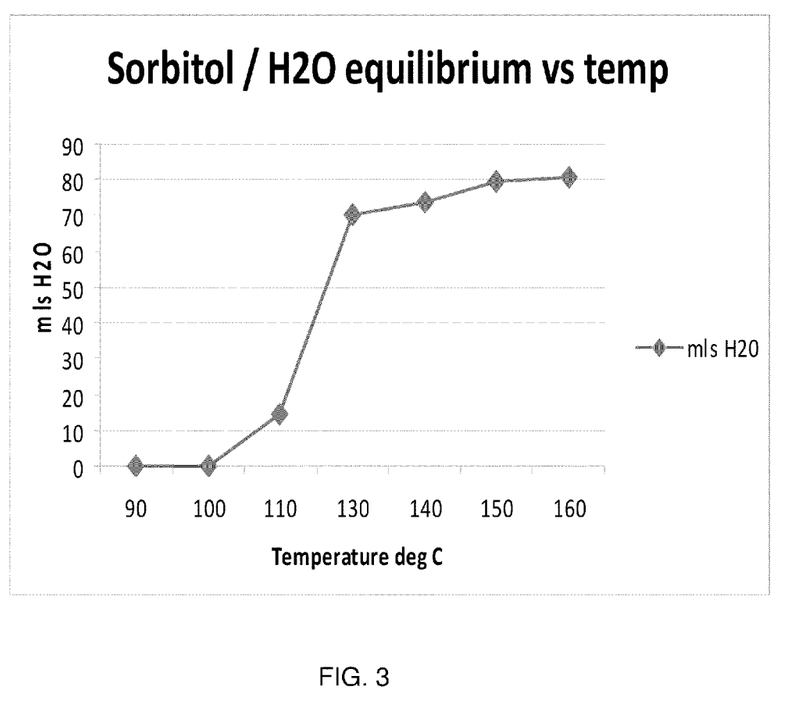
FIG. 3 is graph of the level of water evolved from an aqueous sorbitol/water solution over a temperature range of 90° C. to 160° C. (no acid is present so we are examining only the amount of water that is removed by distillation as a function of temperature).

In quantities needed for a commercial-sized facility, sorbitol contains a high amount of water. An experiment was carried out with a solution of 70% sorbitol in water to monitor the removal of water at ambient pressure from the reaction vessel over time as the temperature was increased from 90° C. to 160° C. The results are shown in FIG. 3.

Example 4

In this example, 70% sorbitol in water was added to the reaction vessel together with 1% acid by weight (relative to the amount of sorbitol). The reaction vessel was maintained at ambient or atmospheric pressure while heated using the temperature profile set out in Table 1.

TABLE 1

Temperature Profile

| Time (minutes) | Temperature (° C.) |
|---|---|
| 60 | 111 |
| 120 | 116 |
| 180 | 126 |
| 240 | 139 |
| 300 | 153 |

Figure 4:
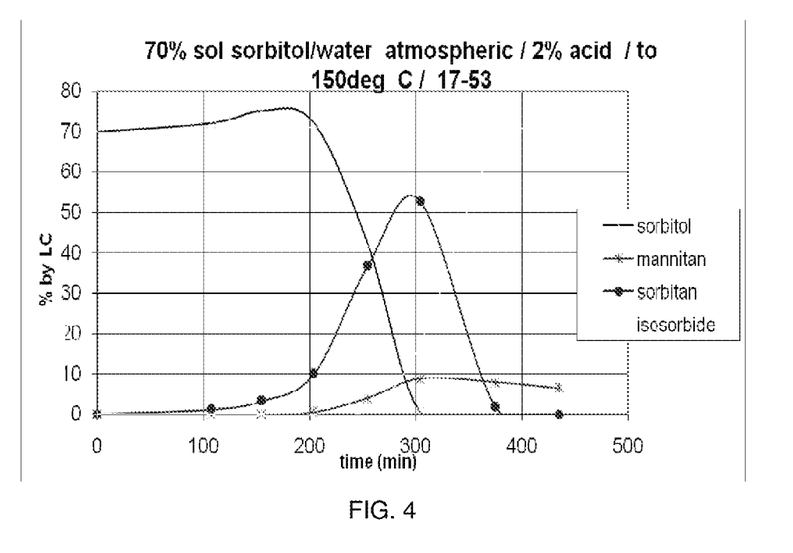
FIG. 4 is a graph of the production of isosorbide from sorbitol, including the intermediary sorbitan and the side reaction product, mannitan, run at ambient pressure as the temperature is increased to 150° C. over 450 minutes.

Samples were taken at regular intervals and assayed for sorbitol, sorbitan, mannitan and isosorbide. The results are shown in FIG. 4. It was observed that almost no reaction occurs until a temperature of approximately 125° C. is reached (approximately 180 minutes). Up to that point, water is being removed from the sorbitol and therefore the sorbitol concentration and acid strength are increasing. At about this point, the conditions, including sorbitol concentration, acid strength, and temperature, are such that the reaction starts occurring at a significant rate. In another hour (240 minutes and 139° C.) the reaction is occurring at a reasonable rate and about half of the sorbitol has reacted but there is still only a small amount of isosorbide. After another hour (300 minutes and about 150° C.) the reaction is proceeding at a rate that is comparable to that obtained with a reaction at 125° C. and full vacuum (Example 1).

Example 5

Figure 5:
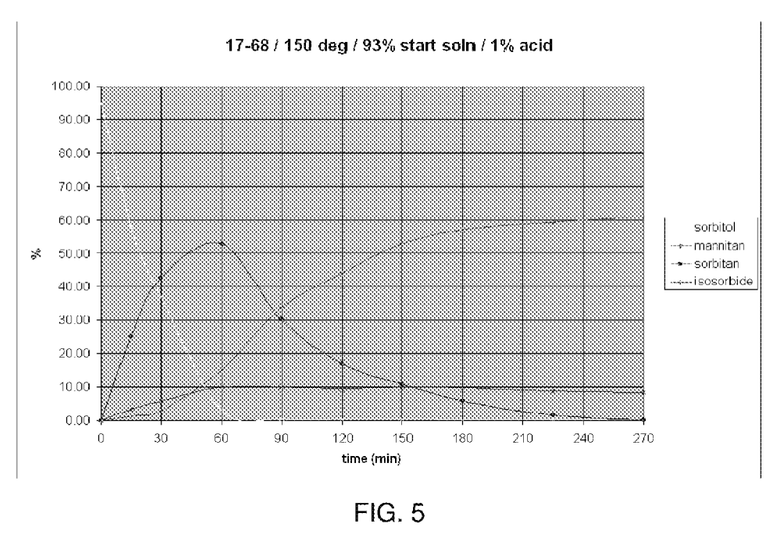
FIG. 5 is a graph of the production of isosorbide from sorbitol, including the intermediary sorbitan and the side reaction product, mannitan, run at ambient pressure where the water content of the starting sorbitol has been reduced.

In this example, the reaction was carried using a melt of dry sorbitol (93% sorbitol in water). Alternatively, sorbitol available on a commercial scale can be dried by removing the water in a separate step. Sulfuric acid (1% relative to the sorbitol) was added, and the reaction vessel heated to 150° C. Samples were taken at regular intervals and assayed for sorbitol, sorbitan, mannitan and isosorbide. The results are shown in FIG. 5. Again, the reaction at atmospheric pressure and 150° C. was observed to run at a similar rate to one under full vacuum at 120° C.

Example 6

A series of reactions were carried out under the conditions set out in Table 2. All of the reactions carried out at atmospheric pressure provided a higher yield of isosorbide than the reaction run under vacuum (Example 1).

TABLE 2

Yield of Crude Product

| Conditions | Yield of Crude Product[1] |
|---|---|
| Ramp to 150° C.; 1% acid; atmospheric | 69.9 |
| Ramp to 150° C.; 1% acid; atmospheric | 69.5 |
| Ramp to 150° C.; 1% acid; atmospheric | 69.5 |
| Constant 150° C.; 1% acid; atmospheric | 68.6 |
| Constant 125° C.; 1% acid; vacuum | 66.2 |

[1]Defined as weight of sorbitol vs. weight of isosorbide (note that commercially available sorbitol contains some manitol).

Example 7

A 70.78% sorbitol solution in water (analysis by Karl fisher determination) in the amount of 50,172 grams (corresponding to 35,512 grams of contained sorbitol) was charged to a flask and heated to remove 11,883 grams of water. At this point 349 grams of sulfuric acid was added and the flask slowly heated to 150° C. and held at this temperature while the evolved water was collected. After the reaction was completed (indicated by the absence of further water evolution) the crude material was distilled to give four fractions containing a total of 19,427 grams of crude isosorbide. These fractions ranged from about 98 to about 99% pure with almost another 1% of the other 2,6 dianhydrosugars also present. When we correct for the purity of the distilled samples we find that they contained a total of 19,100 grams of pure isosorbide. The residue was found to contain another 1,617 grams of isosorbide to give a total amount of isosorbide produced of 20,717 grams. This corresponds to a chemical yield to isosorbide of 72.72%. However, we know the purity of the starting sorbitol is only 96.58% which means we actually had only 34,297 grams of sorbitol at the start of the reaction and the chemical yield based on that value is 75.30%.

Example 8

The preparation of isosorbide can also be carried out in a Continuous Stirred Tank Reactor system (CSTR). The concept is that starting materials are fed to a reactor system while, at the same time, product is being removed. The system can also be set up so material flows from one reactor to another so, for example, the early part of a reaction can be carried out at a low temperature while the further reaction can be completed at a higher temperature. We used a number of different systems and our example will be with 3 reactors of the same size operating in series. A continuously weighed acid resistant 5 gallon plastic feed tank fitted with a constant temperature bath controlled coil. A 70% water solution of sorbitol containing 1% H2SO4 based on sorbitol was held at approximately 40° C. to help prevent crystallization and skin formation. A jacketed feed line was connected to a positive displacement pump with a water washed piston to prevent the pump from binding. A feed rate of 8 grams per minute was typical. Feed entered the first of three one liter glass CSTRs via a dip tube. Each CSTR was heated independently by controlled electric heating mantle and was fitted with a cold water condenser. Flow from one CSTR to the next was by gravity fed via an overflow side port having a u trap to prevent water vapor from continuing downstream. Overhead condensate was collected and measured. Typical CSTR temperatures were on the order of 135, 150, and 150° C. A continuously weighed 5 gallon plastic receiving tank collects product exiting from the final reactor. Typical product recovery is on the order of 5 grams per minute. When this crude material was distilled the chemical yield to isosorbide was found to be 70.9%.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A process for the production of a dianhydrosugar isomer from a sugar alcohol via the sugar alcohol anhydride intermediary, comprising the steps of:
   (a) combining a sugar alcohol with between about 0.1% and about 5% by weight of an acid catalyst to create an organic solvent-free reaction mixture;
   (b) heating the reaction mixture under ambient pressure conditions to a temperature of between about 130° C. and about 170° C. to remove water generated in the formation of a sugar alcohol anhydride intermediary without assistance of an inert gas purge;
   (c) holding the reaction mixture at a temperature of between about 130° C. and about 170° C. until less than a preselected amount of the sugar alcohol anhydride intermediary remains yielding the dianhydrosugar isomer at 98% or greater purity.

2. The process as defined in claim 1, wherein the sugar alcohol is selected from the group consisting of sorbitol, mannitol and iditol.

3. The process as defined in claim 1, wherein the acid catalyst is selected from the group consisting of sulfuric acid, phosphoric acid; alkyl, aryl, and arylalkylsulfonic acids; polymer bound sulfonic acids; trifluoromethanesulfonic acid; strong acid resins; acid forms of perfluorinated membranes; heteropoly acids and their acidic salts; zeolites; and acid clays.

4. The process of claim 1, wherein the concentration of the acid catalyst is between about 0.5% and about 2.5%.

5. The process as defined in claim 1, wherein the temperature is held at a constant value throughout the process.

6. The process as defined in claim 1, wherein the temperature is increased during a portion of the process.

7. The process as defined in claim 1, wherein the temperature of the reaction mixture is different in a first portion of the process and in a second portion of the process.

8. The process as defined in claim 1, wherein the sugar alcohol is sorbitol and the acid catalyst is sulfuric acid.

9. The process as defined in claim 8, wherein the temperature of the reaction is between about 140° C. and about 155° C.

10. The process as defined in claim 8, wherein the sorbitol is combined with between 5% and 60% water to form a sorbitol solution.

11. The process as defined in claim 8, wherein the water content of the sorbitol solution is reduced prior to addition of the acid catalyst.

12. The process as defined in claim 8, wherein the temperature is adjusted to maintain a preselected sulfuric acid/water concentration.

13. A process as defined in claim 1 in which the reaction is carried out in one or more continuous stirred tank reactors.

14. A process as defined in claim 1 wherein the reaction is heated to between about 140° C. and about 170° C. and held at between about 140° C. and about 170° C.

15. A process for the production of a dianhydrosugar from a sugar alcohol via the sugar alcohol anhydride intermediary, comprising the steps of:
   (a) combining a sugar alcohol with between about 0.1% and about 5% by weight of an acid catalyst to create an organic solvent-free reaction mixture;
   (b) heating the reaction mixture under ambient pressure conditions to a temperature of between about 130° C. and about 170° C. to remove water generated in the reaction mixture without assistance of an inert gas purge to convert the sugar alcohol into the dianhydrosugar without any intermediary other than the sugar alcohol anhydride intermediary; and
   (c) holding the reaction mixture at a temperature of between about 130° C. and about 170° C. until less than a preselected amount of the sugar alcohol anhydride intermediary remains.

* * * * *

UNITED STATES PATENT AND TRADEMARK OFFICE
CERTIFICATE OF CORRECTION

| | |
|---|---|
| PATENT NO. | : 9,120,806 B2 |
| APPLICATION NO. | : 12/421514 |
| DATED | : September 1, 2015 |
| INVENTOR(S) | : David James Schreck et al. |

It is certified that error appears in the above-identified patent and that said Letters Patent is hereby corrected as shown below:

IN THE SPECIFICATION

Column 1, line 6, please insert the following:

--GOVERNMENT SUPPORT
This invention was made with government support under Grant Number: 2009-10002-05143 awarded by the National Institute of Food and Agriculture within the U.S. Department of Agriculture. Accordingly, the government has certain rights in this invention.--

Signed and Sealed this
Twenty-third Day of August, 2016

Michelle K. Lee
*Director of the United States Patent and Trademark Office*